United States Patent [19]

Klebe

[11] Patent Number: 5,108,926

[45] Date of Patent: Apr. 28, 1992

[54] APPARATUS FOR THE PRECISE POSITIONING OF CELLS

[75] Inventor: Robert J. Klebe, Helotes, Tex.

[73] Assignee: Board of Regents, the University of Texas System, Austin, Tex.

[21] Appl. No.: 94,341

[22] Filed: Sep. 8, 1987

[51] Int. Cl.$^5$ .......................... C12M 3/00; A61F 2/10
[52] U.S. Cl. ................................ 435/284; 435/292; 435/299; 435/240.23; 435/240.243; 427/2; 600/36; 623/15
[58] Field of Search ................ 435/30, 284, 285, 287, 435/292, 293, 297, 299, 300, 240.243, 240.23; 346/140 R; 118/715, 64, 313; 401/35; 427/2, 4; 600/36; 623/66, 15

[56] References Cited

U.S. PATENT DOCUMENTS

| | | | |
|---|---|---|---|
| 4,656,130 | 4/1987 | Shoshan | 435/30 |
| 4,664,945 | 5/1987 | Maeda et al. | 346/140 R |
| 4,791,069 | 12/1988 | Hovarka et al. | 427/2 |
| 4,874,500 | 10/1989 | Madou et al. | 204/408 |
| 4,877,745 | 10/1989 | Hayes et al. | 346/140 R |

OTHER PUBLICATIONS

Klebe et al. (1987), "Fibronectin,—Mediated Attachment of Mammalian Cells to Polymeric Substrata", Chapter 38 of Proteins at Interfaces, ACS Symposium Series 343, eds. Brush and Horbett, pp. 615-628.

Klebe et al. "Adhesive Substrates for Fibronectin", Journal of Cellular Physiology, vol. 109, pp. 481-488 (1981).

Primary Examiner—David L. Lacey
Assistant Examiner—William H. Beisner
Attorney, Agent, or Firm—Arnold, White & Durkee

[57] ABSTRACT

Disclosed are apparati for the precise positioning of cells into highly organized tissue structures. In particular, ink jet printers and graphics plotters are modified to allow their use in the preparation of tissue structures which are suitable for use in the treatment of burn patients. Cells are positioned by the use of computer-controlled placement of cell adhesion materials such as fibronectin to a substratum which is suitable for maintaining cell growth, followed by allowing cells to attach to those areas of the substratum where the cell adhesion material has been placed. Alternatively, specific placement of cells onto substrata is obtained by the computer-controlled placement of cells directly. These apparati may be even further modified and improved by providing a controlled biological environment in the area of the substratum, thus providing an integral unit for the production of organized tissues.

13 Claims, 6 Drawing Sheets

A

APPARATUS FOR THE PRECISE POSITIONING OF CELLS

The Government may have certain rights in the present invention pursuant to NIH grant CA33074.

BACKGROUND OF THE INVENTION

1. Field of the Invention

The present invention relates to methods and apparati for the precise positioning of cells in a selected array or pattern on a separable substratum. More specifically, the invention relates to methods and apparati for preparing tissues, and in particular, human tissues, having a precisely controlled cellular organization.

2. Description of the Related Art

The ability to prepare organized tissues or tissue-like structures starting with individual cells or colonies of cells is a science that is still in its infancy. However, tissue and even organ culture has progressed to a point such that it is now possible to routinely layer individual cells or colonies of most any particular cell type or types onto an appropriate solid matrix, and grow the layered cells in an appropriate medium until a randomly organized "tissue" is obtained. Although such tissues have a potentially wide range of usefulness, their primary utility has been in the field of tissue transplantation or replacement, for example, in plastic surgery and tissue reconstruction.

Tissue reconstruction employing tissues formed from cultured cells has found its most widespread application in the context of burn patient treatment. Traditionally, the treatment of burn victims has consisted primarily of debridgement of the dead tissue, maintaining a sterile moist environment around the affected area, and allowing the body to produce scar tissue While effective under optimal circumstances, such treatments suffer from potentially serious drawbacks due to the difficulty in maintaining the affected area in a sterile, moist environment. This inability can lead to serious repercussions such as severe infection, the leading cause of death in burn patients who survive the initial burn trauma.

More recently, attempts have been made to improve the treatment of burn patients through the use of a sterile layer of skin tissue that is grown in vitro and transplanted to cover the burned tissue. Such transplanted tissues serve the dual purpose of both protecting the affected area, by providing a physical barrier to infection, as well as aiding in maintaining the burned tissue in a humidified state. In such methods, cultures of freshly explanted dermis, preferably from the affected patient to be treated, are prepared by explanting dermal tissue, dissociating the tissue into individual cells, and culturing the dissociated cells in vitro to form a "tissue" layer. Once an integral tissue layer is obtained, it is transplanted to the burn patient to cover the affected area. While certain problems are addressed by this technique, including in particular, problems associated with tissue rejection, the method nevertheless has serious drawbacks. Most notable of these drawbacks is the inability to precisely structure and organize the cultured tissue in that many cell types are randomly positioned with respect to each other. Accordingly, the normal arrangement of cells in a normal tissue is generally not reproduced in the grafted tissue which can lead to a grafted tissue that is not normal in appearance, often colorless or blotched.

Accordingly, there is currently a need for novel approaches to the construction of transplantable tissues or tissue-like structure which would allow the precise positioning of cells into organized tissue structures for subsequent transplantation. Moreover, there is a need to provide techniques and apparati which allow the orderly and reproducible formation of transplantable tissues into structures suitable for application to burn victims, for the production of synthetic veins or even organs, or other medical uses.

SUMMARY OF THE INVENTION

Accordingly, it is an object of the present invention to provide methods and apparati which address at least some of these or other deficiencies in the art by allowing the precise positioning of cells to thereby form highly organized tissue structures.

It is an additional object of the invention to provide techniques suitable for the production of tissues for surgical application and, in particular, epidermal tissues for application in the treatment of burn patients.

It is a more particular object to provide techniques and apparati for the cellular arrangement of tissues by the computer-controlled construction of two or three dimensional tissues of virtually any cell type and/or configuration.

Accordingly, the invention, in its most general and overall scope, is concerned with methods and apparati for precisely locating cells on a separable substratum As used herein, a "separable substratum" is defined as a solid matrix upon which cells may be grown. The matrix is separable in that it may be readily removed from underlying solid supports and freely transported. Moreover, in certain embodiments, the substratum is separable in that it is made of a material or treated in a manner such that, once cells have been positioned thereon and allowed to integrate into a tissue, the resultant tissue is separable from the substratum if so desired.

The invention thus embodies the realization that cells may be precisely positioned with respect to each other on a substractum, held in specific relative position by a cellular "glue" substance, and the cells allowed to grow together into a cohesive "tissue". Through the precise positioning of cellular glues, referred to herein as cell adhesion substances, or by precise positioning of the cells directly, cells are arranged with an accuracy of within that of a cells diameter.

In certain embodiments, the invention is directed to an apparatus for positioning cells. The apparatus, in a general sense, embodies a solid support, a separable substratum layered on the solid support, container means connected to the support, for containing the cell adhesion material or cells, and positioning means, connected to the support and container means, for positioning cell adhesion material or cells at selected points within an array.

As used herein, the phrase "selected points within an array" is meant to refer to points in an ordered geometric matrix, whether a two-dimensional or three-dimensional matrix. Accordingly, positioning at selected array points refers to an orderly reproducible placement which, for example, may be defined mathematically and stored in computer memory. Such positioning, therefore, generally cannot be obtained entirely by human hands, in that manual positioning is not sufficiently reproducible or rapid to allow the successful orderly layering of tissue components.

The cell adhesion materials of the present invention are molecules having an ability to bind to cell surfaces Numerous such molecules are known in the art, from various classes of agents. For example, the most useful overall cell adhesion substance is fibronectin, a protein having a particular affinity for a specific cell-surface binding site on virtually all cells. Accordingly, fibronectin, which is readily available to the art, serves as a useful cell gluing substance in the practice of the invention. However, it will be appreciated that the invention is in no way limited to fibronectin in that numerous useful adhesion substances are available to the art, including laminin, chondronectin, epinectin, epibolin, uromorulin and other cell adhesion proteins.

Moreover, in certain embodiments, it may be more convenient and/or advantageous to employ substances having a more particular affinity for specific cells and/or cell types. In such instances, it is desirable to use antibodies that specifically recognize an antigenic determinant on the surface of the desired cell type. In these instances, an appropriate of the antibody is positioned on the substratum and subsequently contacted with a cell suspension which includes the appropriate cell type to allow specific attachment of the cell type to the emplaced antibody.

The particular type or means of solid support is not crucial and may take any of a variety of forms or materials, so long as it serves to maintain the substratum in a suitably firm, relative placement during positioning of the cells or cellular adhesion material. It will often be the case that the support will be in the form of a platform contained within a biologically controlled environment. In this manner, an apparatus may be produced that embodies the invention in a self-contained structure, i.e., an apparatus which allows both the positioning of cells in one of various ways, as well as culturing of the positioned cells sufficiently to form a transportable tissue.

Similarly, a container means is provided that is designed for containing a working aliquot of cell adhesion material or cells. Typically, the container means will be in the form of a vessel that will contain the aliquot in a relatively isolated state, generally free of contamination such as debris or microbial growth. The container means is connected to the solid support in a manner which allows communication between the container and the positioning means. For example, the container may be attached to the positioning means by a tube or passage which allows fluid communication with the positioning means. Moreover, in certain embodiments, the container means may be placed directly adjacent to or within housings employed for delivery of biological substances in connection with the positioning means.

The positioning means is, in a general and functional sense, a structure which allows the specific positioning of biological materials such as cells or adhesion materials. Structures serving such a function may take a number of forms. For example, positioning may be accomplished through the use of a mechanically controlled application arm whose movements are reproducibly controllable and, preferably, rapid and precise. In such an embodiment, the means would typically include a housing for receiving a flow of cell surface adhesion material or cells from their respective containers and depositing the material on the substratum. The housing includes at least one metered pore through which the material would flow out of the housing and onto the substratum. By "metered" is meant that the flow of material through the pore is controlled, whether at the pore itself, as with an electrostatic or capillary attraction control, or in connection with a controlled rate of supply of the material from the container means.

Positioning is preferably accomplished through the use of a housing structure having a plurality of pores, wherein each of the pores are individually metered. In this manner, positioning is achieved by directing the flow of cells or adhesion material through selected pores, with the opening and closing of pores acting much like a "stencil".

In either case, data processing means is typically employed to control the movement of the housing and/or metering of the pores. Through data processing techniques, a level of positioning control and speed is achieved such that an orderly and reproducible placement of material is realized in a period of time which is sufficiently short so as to render tissue construction in accordance herewith both economical and practical.

Useful substrata in accordance with the present invention are of three general types. In certain embodiments, substrata are employed to which cells will not attach, wherein the substrata has been treated with a coating of heat-inactivated protein such as albumin or virtually any other denatured protein. Such substrata are referred to herein as "negative-image" substrata in that because cells will not attach to the surfaces in the presence of heat inactivated protein, a negative image (i.e.-no growth) will be provided on the resultant surface. However, when these substrata are treated with cell adhesion material at selected points, they become adhesive to cells, even in the presence of heat-inactivated albumin, and thus become "positive-image" substrata at such positions which receive the adhesion material. Useful substrata which, in accordance with such embodiments may variously serve as both positive or negative image surfaces, include numerous polymers, plastics, ceramics, metals or the like, including such materials as polystyrene, polymethylmethacrylate, poly-vinylchloride, polyvinylacetate, Teflon ®, cellulosics, pyrex glass, Carnauba wax, silicone, aluminum, culture plates, etc. Accordingly, depending on whether such materials are coated with heat inactivated protein, or alternatively one of the cell adhesion materials, the surface will be rendered either adhesive or non-adhesive to cell growth.

A second class of substrata are those to which cells will attach even following treatment with heat inactivated albumin. A preferred substrata of this class is collagen. Due to the specific interaction of the cell adhesion material with receptors on collagen, cells will attach to collagen in the presence of cell adhesion material even following treatment with heat inactivated albumin Other substratum which will bind cell adhesion material and hence support cell growth even in the presence of albumin includes gelatin and synthetic collagen peptides.

A third class of useful substratum in accordance with the present invention include materials to which cells will not attach even in the presence of fibronectin, or one of the other cell adhesion materials, as well as in the presence of heat-inactivated albumin. Such surfaces include agar, and agar derivatives such as agarose or Sepharose ®, polyhydroxyethyl methacrylate, to a certain extent polyacrylamide and, of course, bovine serum albumin itself.

Accordingly, one will desire to choose one of the foregoing class of substrata depending on the particular circumstance, i.e. whether one desires cell attachment ("positive image") or non-attachment ("negative image"). In this manner, the various surfaces, or surface treatments (e.g., coating with albumin), may be employed to obtain a selected placement of positive and negative "images", allowing the orderly arrangement of cells of differing types within the resultant tissue structure. For example, by specific placement of fibronectin at particular locations on a fibronectin-binding surface, followed by treatment of the surface with heat-inactivated albumin, cells will attach only to those positions containing fibronectin, thus providing a "positive" image at such points. Where collagen is used as a substratum, there is no need to pre-coat the surface with denatured protein in that cells will not directly attach to collagen. Thus, where collagen is employed as the substratum, negative areas may then be filled in by reapplication of cell adhesion materials followed by layering of a second cell type.

Surfaces of the third type (i.e., those that will not bind cells even in the presence of cell adhesion material) are particularly useful in connection with cytoengraving embodiments of the present invention. In cytoengraving, a substratum such as agar is employed and a cell attachment surface such as those that will bind cells in the presence of fibronectin is applied to the nonattachment surface agar at locations where cell attachment is desired. In this manner, the agar surface is "stenciled" with a pattern to allow specific cell attachment to the pattern while leaving the background agar free of cell growth. Then, by removing the agar coating from various remaining positions, cell attachment may be achieved to such positions where the surface which underlies the agar is a cell attachment surface (i.e., a cell adhesion material-binding surface).

Accordingly, the present invention presents a method for precisely locating cells on a substratum which includes the steps of layering a separable substratum on a solid support, stenciling the substratum by positioning cell adhesion material at selected points within an array on its surface, obtaining a suspension of cells, and contacting the stenciled substratum with the cell suspension to allow adherence of the cells to the positioned cell adhesion material. The separable substratum will generally be one of the foregoing general types including, for example, collagen, pyrex glass, agar, gauze, or any of the other foregoing adhesive or non-adhesive surfaces, depending on the application.

Stenciling the substratum will generally include precisely locating a housing at computer specified array points over the surface of the substratum, the housing receiving a flow of cell surface adhesion material on the substratum, and having at least one metered pore through which the material may flow onto the substratum. However, preferably the housing has a plurality of metered pores, the flow of material through the pores being selectively metered to allow a selected positioning.

In certain particular embodiments, a method for cytoengraving is provided for precisely locating cells, the method including the steps of layering a separable substratum on a solid support, layering the substratum with a photopolymerizable monomer, stenciling the substratum by photopolymerizing the monomer in a desired pattern, washing the substratum to remove unpolymerized monomer, coating the monomer-stenciled substratum to prevent the adherence of cell adhesive to the monomer stencil, layering the coated substratum with a cell adhesion material, obtaining a suspension of cells, and applying to the stenciled substratum a cell suspension to allow adherence of the cells to the treated region of the substratum. Particularly useful photopolymerizable monomers include both positive and negative photoresist materials.

DETAILED DESCRIPTION OF THE PREFERRED EMBODIMENTS

The present invention relates to a novel technique, termed "cytoscribing", which is designed to enable one to establish precise spatial interrelationships between cells. In essence, cytoscribing involves the use of a computer for the high precision positioning of cells into predetermined patterns. It is demonstrated that patterning devices commonly employed in the printing or computer graphics industry, such as an ink jet printer or graphics plotter, may be employed to position cells, either by position cell adhesion materials, or the cells themselves, onto a suitable substratum. In addition, a cytoengraving method, similar in approach to photoengraving techniques used in the silicon chip industry, is disclosed. This technique is employed to position cells to within a micron of a desired location. By utilizing and combining the various embodiments disclosed, positive and negative patterns of cells (termed "cytoscripts") may be achieved, allowing the precise construction of two and three dimensional tissues.

Figure 1:
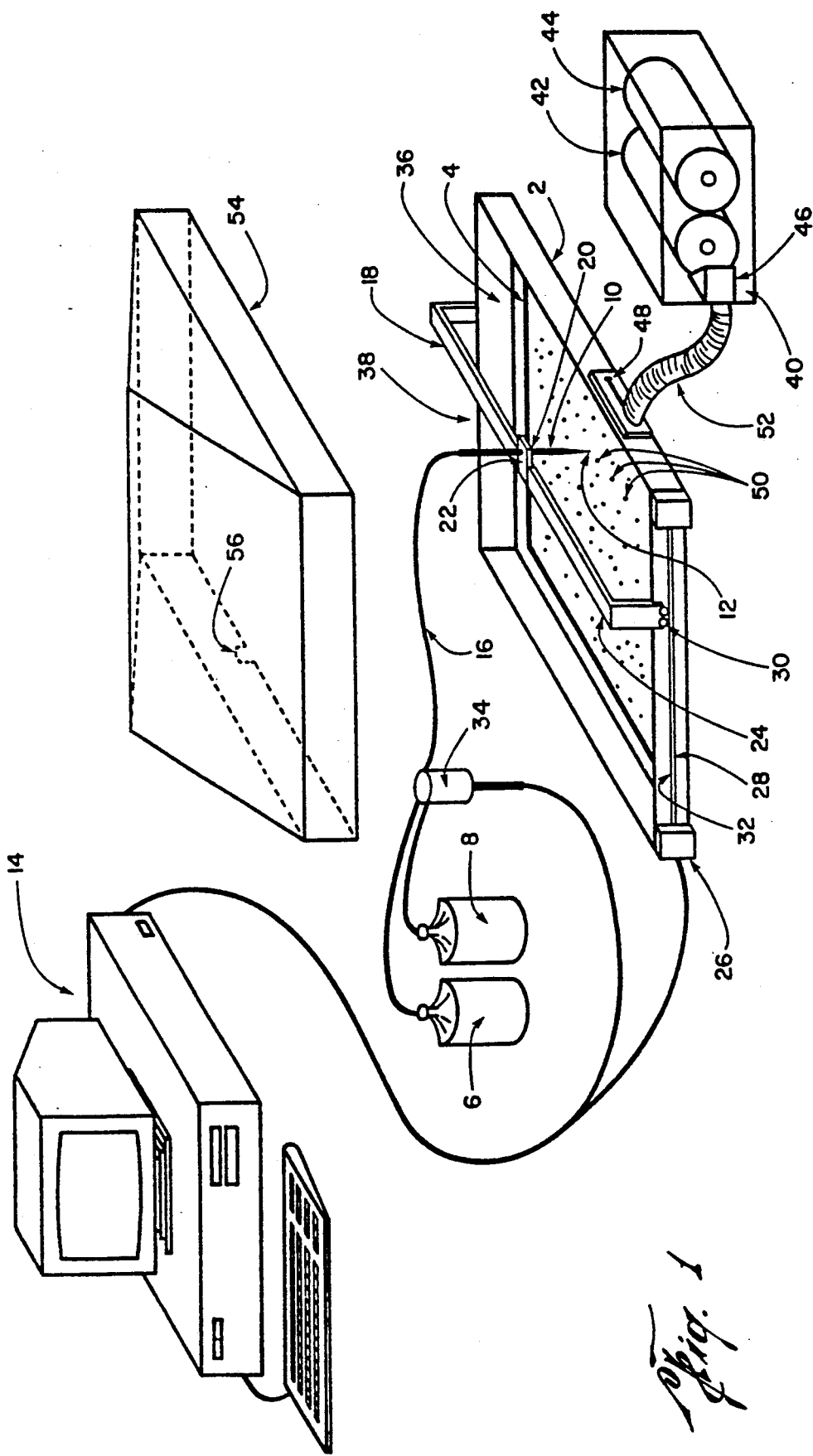
FIG. 1 shows a full view of an apparatus in accordance with the present invention.

Turning now to FIG. 1 is shown an apparatus in accordance with the present invention. As illustrated, the apparatus includes a solid support 2 on which is layered a separable substratum 4. First container means 6 is provided for containing a cell adhesion material, or alternatively or in addition, a second container means 8 is provided for containing cells or other materials to be applied to the substratum. A positioning means 38, connected to the support 2 and in fluid communication with container means 6 and/or 8, is provided for positioning cell adhesion material or cells at selected points within an array on the surface of the substratum 4.

In the embodiment displayed in FIG. 1, the positioning means 38 includes a housing 10 that is provided for receiving a flow of cell surface adhesion material from the first container means 6, or cells or other materials for application from the second container means 8, and for depositing the received material onto the substratum 4. The housing 10 shown in FIG. 1 is a standard graphics plotter pen which has been modified in the manner discussed below. However, housing mounting 20 may be readily adapted to receive an alternative printing housing such as an ink jet printer or similar structure.

The housing 10 includes at least one pore 12 through which material may flow onto the substratum 4. However, where the printing housing employed is, e.g., an ink jet printer (FIG. 2), it will typically include a plurality of computer-controlled metered pores 12. In either case, a data processor 14 is provided which directs the positioning of the housing 10 at selected array points over the surface of the substratum 4. The housing 10 is in fluid connection with container means 6 and/or 8 by means of channel 16, through which material is provided to the housing 10. In operation, the data processor 14 directs the movement of a transit arm 18 in lateral or forward or backward directions, thus delivering a flow of cell adhesion material to selected computer-directed points.

In the embodiment shown in FIG. 1, the housing 10 is located by mounting 20 which is slideably attached to guide 22. Guide wires 24, attached to mounting 20, are actuated by computer-controlled motors 26 to position the mounting 20, and hence housing 10, in forward and backward directions ("Y-axis"). Transit arm 18 itself is slidably attached to the support 2 by means of carriage 30 along rails 28. Computer-controlled guide wires 32 control the lateral position of transit arm 18 ("X-axis" locations).

Also shown in FIG. 1 is a computer-controlled metering device 34 for selectively controlling the flow of material from container 6 or 8. Metering device 34 may further include a pump device, such as a peristaltic pump, to provide additional flow capability where desired. Biological control of the environment with the cell growth area 36 of the apparatus is provided by environmental control device 40. The environmental control device 40 includes atmosphere control cylinders 42 and 44 (including generally $CO_2$ and air). Environmental control device 40 will generally further include a temperature control function including heater 46 and temperature sensor 48. Biological control may be manual or computer directed as desired. In operation, air in the form of a 5% CO in air mixture, is fed to cells 50 growing in cell growth chamber 36 by means of channel 52. Also, cover 54 is provided to assist in maintaining biological control. During periods of cell growth line 16 may be detached, or alternatively, opening 56 is provided.

One type of housing 10 for the application of adhesion material to the substratum found to work well in connection with the present invention is a so-called plotter pen. Where a plotter pen is employed, it will be appreciated that computer control will be limited to directioning of the housing 10 (in this case the pen) by means of transit arm 18, in that there is no computer-controlled pores on the felt pen tip. In the case of a plotter pen, metering of flow through the pen and onto the substratum is obtained generally by the degree of downward pressure applied by transit arm 18 or alternatively by pump 34.

A plotter pen and apparatus which has been modified to allow the practice of the present invention is Hewlett Packard 747A graphics plotter. In order to insert fibronectin into the Hewlett Packard plotter pen, the plastic cap of a pen was dislodged, the ink containing absorbent material discarded, and ink was removed by passing a copious amount of ethanol through the pen tip. The felt tip was then washed with distilled water and dried. Absorbent cotton was placed inside the pen housing and 200 ug/ml fibronectin in 0.15 M NaCl +0.1 M Imidazole, pH 6.95, was added to the pen. The fibronectin loaded pen could be used for at least 72 hr; however, it was generally used immediately and then cleaned by rinsing with saline.

Figure 2:
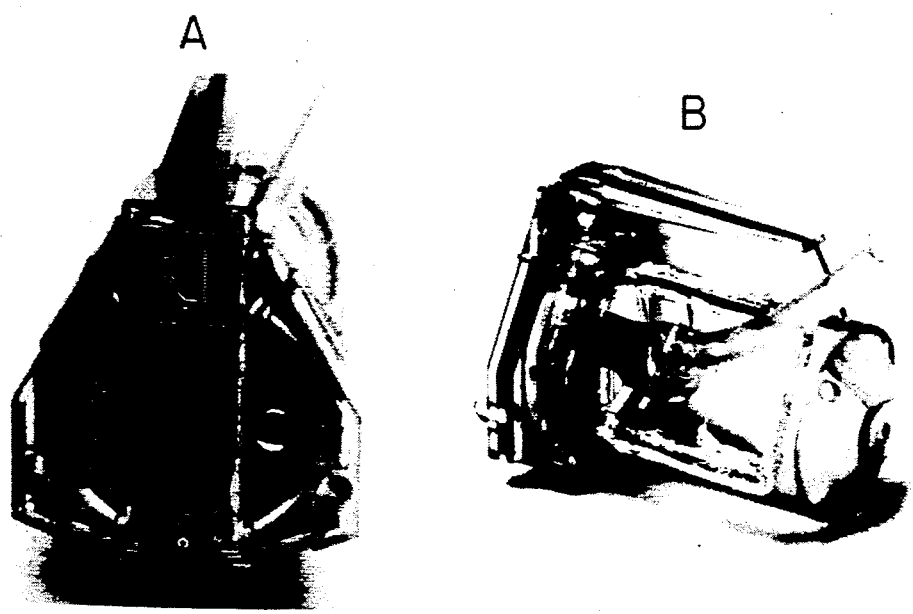
FIG. 2 shows an end view (A) and side view (B) of a housing for application of materials to substrata in accordance with the present invention.

Another type of housing 10 which may be modified to work well in the practice of the present invention, referred to in the printing art as an ink jet cartridge, is shown in FIG. 2. An ink jet cartridge is a computer-controlled printing head commonly employed in the printing industry. The printing head 32 of such an ink et cartridge includes a plurality of computer-controlled nozzles or pores 12 which are fed cell adhesion material or cells by means of channel 16 from container means 6 or 8. A computer controlled electric field dictates the placement of liquid droplets containing cell adhesion material or cells onto the substratum. In this manner, a computer-controlled fine-tuned application of material to the substratum is obtained, much in the same way that ink is applied by ink jet printers in the form of letters and symbols to printing substrates.

A commercially obtained ink jet cartridge (Hewlett Packard 2225C Think Jet ink jet printer) was prepared for fibronectin application as follows Ink was drained from the cartridge by drilling a hole in the gold rivet on the front face of the cartridge and removing the ink with a syringe. A window was cut in the side of the cartridge with a hot scalpel and the black rubber ink bladder was removed. A piece of silicone rubber tubing was glued into the ink well of the cartridge with silicone rubber glue, and 200 ug/ml fibronectin solution in 0.15 M NaCl +0.1 M Imidazole, pH 6.95+10% dextran (10,000 mw) was injected into the ink well with the aid of a Pasteur pipette The fibronectin solution was injected until some of the solution appeared at the silver printing port of the cartridge. Excess fibronectin solution was wiped off; the Pasteur pipette was removed; and the cartridge was inserted into the apparatus.

The plotter apparatus bearing the modified plotter pen as discussed above was further modified through the application of a polystyrene substratum to the plotter paper support as follows: Polystyrene was dissolved in benzene. The polystyrene solution was then applied to glass and air dried. The solid polystyrene was removed from the glass with a razorblade, treated with sulfuric acid and applied to a paper sheet with office tape.

In use, cell adhesion material is first positioned at locations where attachment of a first cell type is desired. The positioning of the plotter pen is programmed to allow the rapid, reproducible deposition of material in whatever arrangement is required. Where a tissue is being formed for transplantation, one will generally desire to ensure that the distribution of each cell type employed in the final tissue is controlled and even. For example, where the first cell type employed in the construction include melanin-producing cells, one will desire to achieve an even distribution of deposited adhesion material, at a density determined by the desired resultant skin color tone After the cell adhesion material is positioned, where the substratum used is one to which cells normally attach, the surface is treated with a denatured protein, such as denatured gelatin or albumin.

The denatured protein-treated substratum bearing the positioned cell adhesion material is then contacted with a suspension of cells of the type which will be positioned first. After the cells have been allowed to attach to the adhesion-treated substratum, the suspension is drained and the surface washed. A second cell type may then be positioned by repositioning cell adhesion material to locations distinct from, and evenly distributed with respect to, the first positioned cell type. As before, the second cell type is positioned by contacting the substratum with a suspension of the second cell type These steps are repeated until all of the various cell types have been positioned, except for the general epidermal cells Prior to the addition of epidermal cells, or whatever cell type is employed for the general background of the "tissue", the entire remaining substratum is treated with cell adhesion material Then a suspension of the final cell type is applied.

Where one employs different antibodies which recognize cell surface determinants of different cell types as the cell adhesion material, it will be appreciated that the number of steps will be reduced. In such cases, the various antibodies are positioned on the substratum at locations where attachment of the corresponding cell type is desired Thus, for example, one will attach monoclonal antibodies which recognize melanin-producing cells at locations where melanin-producing cells are desired. Then, one would attach monoclonal antibodies at positions where the second cell type is desired, and so on. Finally, cell attachment is achieved by contacting the antibody-positioned substratum with a cell suspension which includes all of the desired cell types.

Where the apparatus is an integral unit such as in FIG. 1, one would want at this point to cover the cell culture chamber and initiate biological control so as to provide standard cell culture conditions. The entire cell-laden substratum is then cultured until the tissue is formed.

It will be appreciated that apparati useful in the practice of the invention are not limited to an integrated structure such as is shown in FIG. 1. For example, one may desire to prepare the substratum in the form of a flexible sheet, which sheet may then be "imprinted" with cell adhesion material by means of a printing head attached to a printer. Of course, the primary distinction between cell adhesion "printers" and printers of the prior art, is the use of cell adhesion fluid in the place of ink. After the substratum "paper" is imprinted with cell adhesion protein, the substratum is contacted with a cell suspension as before.

EXAMPLES

Cell culture. SV-T2, a $SV_{40}$-transformed BALB-3T3 cell line, was obtained from the American Type Culture Collection, Rockville, MD, while HeLa and U2OS osteosarcoma cells were provided by Dr. Charles Gauntt and Dr. Barbara Bowman of the University of Texas Health Science Center at San Antonio. Human A431 cells were obtained from the Wistar Institute, Philadelphia, PA. The cell lines were maintained with Dulbecco's medium containing 10% newborn calf serum plus 100 units/ml penicillin and 100 ug/ml streptomycin. In the studies described below, cells were trypsinized, washed twice with culture medium, resuspended at a cell concentration indicated, and then added to a petri plate containing a substrate cytoscribed with fibronectin. Plastic films were kept submerged by affixing them to the culture dish surface with paraffin wax.

Reagents. Fibronectin was purified from bovine serum by gelatin-Sepharose affinity chromatography as described by Miekka et al. (1982), *Thromb. Res.*, 27:1-14, incorporated herein by reference. Rat tail collagen was prepared as described by Klebe et al. (1974), *Nature*, 250:248-250, incorporated herein by reference. Protein-A-Sepharose purified 425-3K4 monoclonal antibodies against the EGF-receptor were obtained from the Wistar Institute, Philadelphia, PA. All other chemicals were of reagent grade.

Deposition of fibronectin on substrata. Cytoscribing was carried out with either a Hewlett Packard 225C Think Jet ink jet printer or a Hewlett Packard 7470A graphics plotter. In this study, the word "fibronectin" was cytoscribed in fibronectin (a) by using the word processing package, Displaywrite 3, in conjunction with the ink jet printer or (b) by using a plotter controlled by a simple BASIC program.

A fibronectin solution was inserted into an ink jet printer cartridge or plotter pen as described above. Note that the amount of liquid delivered by an ink jet cart-ridge is partially controlled by the viscosity of the fibronectin solution employed.

Preparation of Substrata. While virtually any substrate material can be cytoscribed with the aid of a graphics plotter, the use of an ink jet printer preferably employs a flexible material which can be rolled into the carriage of a printer. Thin, flexible plastics can be prepared for use with tissue culture cells as follows. In brief, a plastic petri plate was dissolved in a suitable organic solvent (e.g., benzene) and recast as a thin film on a pane of glass. Following evaporation of the solvent, the flexible, optically clear plastic film was removed from the glass surface with the aid of a razor blade or similar device. Treatment of the plastic surface with $H_2SO_4$ converts the surface into a suitable substratum for cell culture. In this study, polystyrene petri plates were dissolved in benzene and recast as thin films; however, as discussed above, a wide variety of other plastics, ceramics, metals and the like could be used in similar fashion (e.g., see Bentley et al. (1985), *J. Biomed. Mater. Res.*, 19:757-769).

The positioning of the thin plastic film on the carriage (or platform) of the printing device was carried out by first printing the desired pattern, which was in this study the word "fibronectin", on a piece of paper with ink in the manner normally intended by the printing manufacturer. The plastic film was then positioned with office tape over the ink image of the word "fibronectin" and the paper was inserted back into the printing device exactly as it has been previously. An ink cartridge (or pen) filled with a solution containing fibronectin was then inserted into the printing device and the word "fibronectin" was spelled out in fibronectin by activating the printing device. The plastic film imprinted with fibronectin was removed from its paper backing and affixed to a petri plate surface with paraffin wax. After 10 min or longer, the fibronectin imprinted film was treated for 10 min with 1% heat denatured bovine serum albumin (BSA) in phosphate buffered saline (PBS) in order to prevent attachment of cells to areas of the film not imprinted with fibronectin. Prior to addition of cells, the film was washed twice with PBS. Fibronectin was cytoscribed with a plotter in a similar fashion.

After 1.5 hr, a cytoscribed pattern of live cells was either photographed with phase contrast optics or stained with Wright's stain following fixation with neutral buffered formalin.

Certain substrata were coated with collagen or agarose. In this case, substrata were coated with 1 ml/60 $cm^2$ with either 0.125% rat tail collagen in 0.2% acetic acid or 2% agarose in water.

Optical Microlithography. Glass slides were photoengraved with a polymer by polymerization of a photosensitive monomer. In brief, a glass slide was coated with monomer by immersion for 3-5 sec in Negative Photoresist 752 (KTI Chemicals, Inc., Sunnyvale, CA) followed by removal of the solvent by lyophilization. In order to produce a regular pattern of objects with the dimensions of a cell, the coated glass slide was contact printed with a USAF-1951 target (Rolyn Optics, Covina, Ca) using a 150 Watt Sylvania spot lamp. Exposure was carried out for 1.5 min at a distance of 20 cm and the resulting image was developed according to the instructions of the manufacturer using a xylene developer Treatments of the photoengraved polymer which result alternatively in positive or negative cytoscripts are described.

Construction of three dimensional tissues. Thin collagen gels were formed by the preparation of collagen heat gels in a mold. The molds employed consisted of two siliconized microscope slides separated by a piece of K & E 46-9782 graph paper which had a 65×15 mm rectangle cut out of its center. Collagen gels were formed by adding 3 volumes of 1.8 mg/ml rat tail collagen in 5 mM acetic acid to 1 volume of 600 mM NaCl +120 mM TES +120 mM sodium phosphate (pH 7.3) and warming the collagen to 37° C. (see, e.g., Williams et al. (1978), *J. Biol. Chem.*, 253:6578-6585). The graph paper was saturated with the chilled collagen solution and them applied to a siliconized microscope slide. About 1.5 ml of chilled collagen solution was then added to the slide and a second slide was applied in a fashion that excluded air bubbles. The collagen containing mold was then clamped between two 0.5×0.5 inch lighting louvers and placed in a container of 0.15 M NaCl and incubated at 37° C. for 2-4 hr. The collagen gel was maintained under the saline solution in order to prevent dehydration of the gel; if so stored, gels could be used for at least a week.

In a petri plate containing 1% agarose dissolved in serum-free culture medium, a cavity the size of a microscope slide was prepared to receive the collagen gel. Following molding of a collagen heat gel, the mold was transferred to the agarose containing petri plate and the microscope slides were gently pried apart under complete culture medium. The bottom microscope slide was not removed since it was used to transport collagen cells between containers during a following step. After two washes with 5 ml of complete culture medium (20 min/wash), $2 \times 10^6$ SV-T2 cells were added to the gel and cell attachment was allowed to proceed for 4-16 hr.

Monolayers of cells were glued together with collagen as follows. A rat tail collagen solution in complete culture medium was prepared, as follows: 18 volumes of 1.8 mg/ml rat tail collagen in 5 mM acetic acid +6 volumes of 5×concentrated Dulbecco's medium +3 volumes of fetal calf serum +3 volumes of 10×sodium bicarbonate solution (3.73 g $NaHCO_3$/100 ml) was mixed just before use (in the order presented above) and the solution was maintained at 4° C. Cell cultures were chilled to 4° C. for 20 min before the beginning of the gluing procedure. Culture medium was removed from a monolayer and replaced with the chilled collagen solution (in culture medium) described above. A second monolayer of cells was transported from a petri plate by picking up the underlying glass microscope slide with a pair of forceps. The monolayer was inverted over the collagen solution and the thin collagen gel as eased off the microscope slide onto the collagen solution. The monolayers were gently pressed together with the aid of a microscope sized piece of 1% agarose containing serum free culture medium. The mono-layers were placed in a 37° C. incubator to permit heat gelation of the collagen. After 2 hr, the agarose strip was removed and 5 ml of complete culture medium was added.

Figure 3:
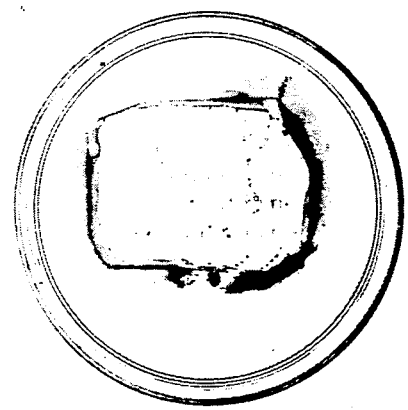
FIG. 3 shows a cytoscribing pattern obtained with the aid of an ink jet printer as described in the text. A piece of plastic cytoscribed with the word "fibronectin" was affixed to the petri plate with paraffin wax and the non-fibronectin treated area was rendered non-adhesive with 1% heat-inactivated BSA. (Panel A): $4 \times 10^6$ SV-T$_2$ cells were applied and unattached cells were decanted after 1.5 hr revealing the word "fibronectin". (Panel B): Under magnification, letters are found to be made up of dots of cells. Each dot is approximately 5 cells wide. The bar represents 100 microns.
Figure 3:
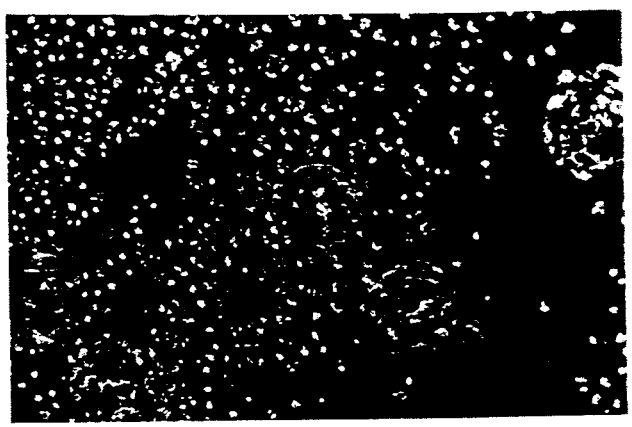

Cytoscribing with an ink jet printer. Details of the use of an ink jet printer in cytoscribing are described above. In brief, a fibronectin solution is sprayed on a surface under computer control to produce a dot matrix (FIG. 3). In initial experiments, it was found that the amount of liquid in a droplet produced by an ink jet printer was determined by the viscosity of the solution employed. A satisfactory result was obtained by using either 50% glycerol or 10% dextran (10,000 mw). When 200 ug/ml fibronectin in 0.15 M NaCl +0.1 M Imidazole, pH 6.95, +10% dextran was applied to a plastic substratum with an ink jet printer and then treated with cells, a pattern of dots about 5 cell diameters wide was obtained (FIG. 3).

Cytoscribing with a graphics plotter. Technical details involved in cytoscribing with a plotter are given in the description of FIG. 4. Briefly, a pen is loaded with a fibronectin solution and a desired pattern is inscribed on a substratum under the control of a computer directed plotter.

Figure 4:
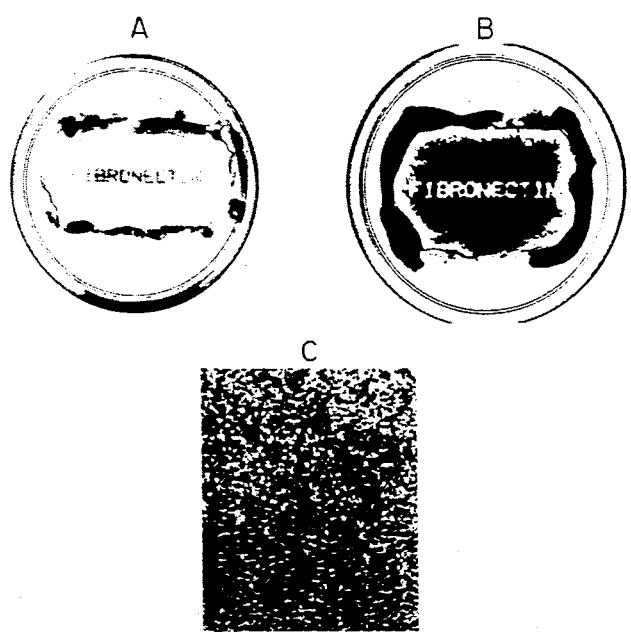
FIG. 4 shows the construction of a two dimensional tissue by cytoscribing. Panel A: A positive image of the word "fibronectin" was produced by cytoscribing a plastic sheet with a plotter pen filled with 200 ug/ml fibronectin. Panel B: A negative image of the word "fibronectin" was produced by (a) removing collagen from a plastic surface with a plotter pen filled with saline, (b) inactivating the exposed plastic with heat-inactivated BSA, and (c) treating the plate with 1 ml of 70 ug/ml fibronectin. In this instance, cells attach to the majority of the plate which remains collagen coated. (Panel C): A two dimensional tissue was constructed by a combination of the techniques displayed in Panels A and B. First, a collagen coated sheet was cytoscribed with a plotter pen containing fibronectin and $4 \times 10^6$ SV-T$_2$ cells. The bottom half of panel C is composed of polygonal HeLa cells while the upper half is occupied by SV-T$_2$ cells.

When fibronectin is inscribed on a plastic surface and the remainder of the surface rendered non-adhesive by treatment with heat inactivated BSA, the word "fibronectin" appears after the surface is incubated with SV-$T_2$ cells (FIG. 4). Using a collagen-coated substratum and a pen loaded with saline, a negative image is obtained by (a) treating the surface with heat-inactivated BSA then (b) incubating the substrate with fibronectin (FIG. 4B). The negative image results from the pen tip physically removing collagen; the BSA makes areas of bare plastic non-adhesive; and, in the final step, the fibronectin renders the collagen adhesive. Thus, both a positive and negative cytoscript can be obtained with the aid of a graphics plotter.

Generation of a two-dimensional tissue. A two dimensional tissue can be produced in two steps similar to that described above for making positive and negative cytoscripts of the word "fibronectin" (FIG. 4A and 4B). In the first step, a fibronectin loaded pen was used to inscribe the word "fibronectin" on a collagen substratum. As in FIG. 4A, the addition of SV-$T_2$ cells results in a positive image of "fibronectin" once unattached cells are removed. Second, treatment of the entire substratum with fibronectin then renders the remaining collagen adhesive for a second cell line (HeLa cells). While HeLa cells attach and spread on the fibronectin-treated collagen, little attachment of HeLa cells to the surface of the SV-$T_2$ cells was noted. Thus, a two-dimensional tissue was constructed by forming positive and negative cytoscripts with two different cell lines on the same substratum (FIG. 4C).

Figure 5:
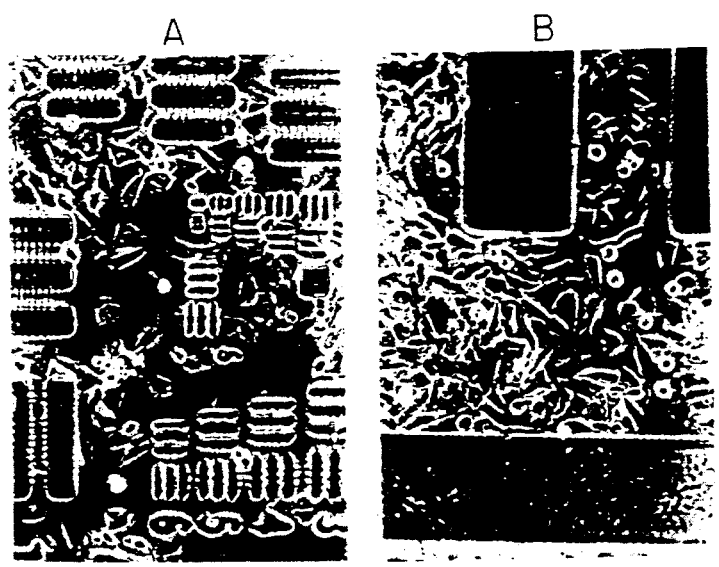
FIG. 5 shows an example of negative cytoscription by photoengraving. A collagen coated glass slide was photoengraved with a polymer as described in the text. The entire slide was treated with heat-inactivated BSA in order to prevent attachment of cells to the polymer. Since BSA treatment does not alter attachment of cells to collagen, cells attach to all regions of the slide except where polymer was deposited. The bar represents 100 microns.
Figure 6:
FIG. 6 shows positive cytoscription by photoengraving. A glass slide was coated with 2% agarose, air-dried, and photoengraved as described in the text. After treatment of the slide with 1 ml 70 ug/ml of fibronectin, cells attached to just those areas photoengraved with polymer. The bar represents 100 microns.
Figure 6:
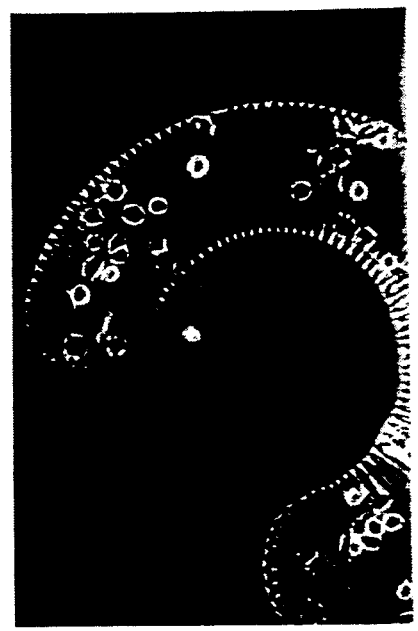

Positive and negative cytoscripts generated by photoengraving technology. As illustrated in FIG. 5A, it is possible to photoengrave substrates with polymeric images that are smaller than the dimensions of a cell. By photoengraving a collagen-coated surface and then rendering the photoengraved polymer non-adhesive by BSA treatment, it is possible to have cells selectively adhere to just the areas of exposed collagen on the substrate (negative image) (FIG. 5). In contrast, a positive image is produced when an agarose treated substratum is photo-polymerized and the deposited polymer is treated with fibronectin (FIG. 6).

Use of monoclonal antibodies in cytoscribing. As demonstrated above, the differential response of cells to substrata treated with cell adhesion proteins can be exploited in cytoscribing. Since only a limited number of cells could be selectively micro-positioned with the use of cell adhesion proteins, the use of monoclonal anti-bodies in cytoscribing was investigated in order to develop a more general method.

Figure 7:
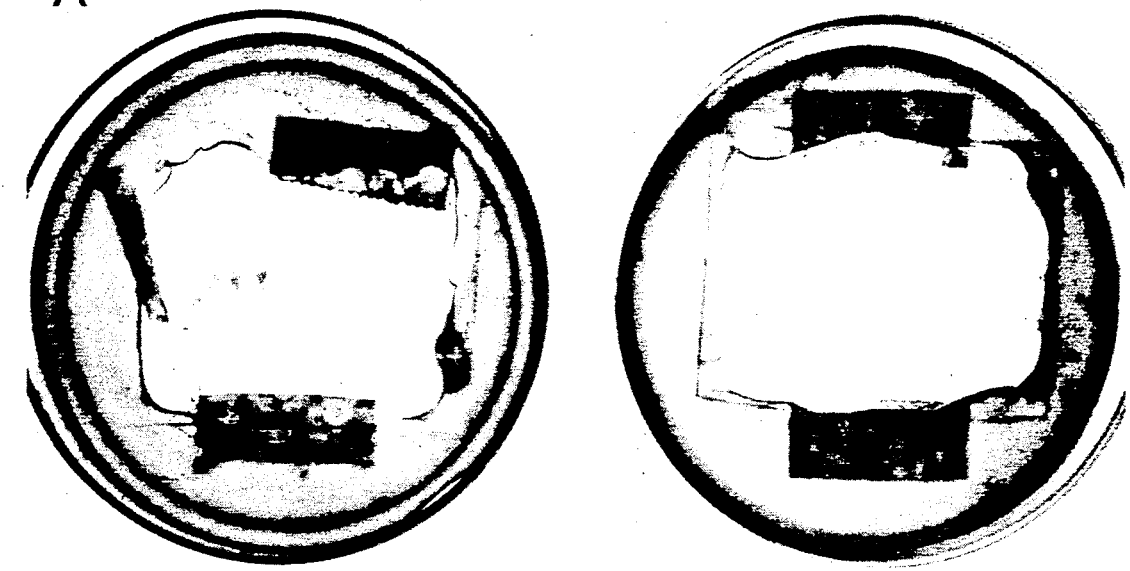
FIG. 7 shows cytoscribing with monoclonal antibodies. Using conditions described below, a plastic surface was cytoscribed with a plotter pen containing 100 micrograms/ml of an anti-human EGF receptor monoclonal antibody. Human A431 cells (left plate), but not mouse SV-T2 cells (right plate), adhered to areas cytoscribed with the anti-human monoclonal antibody.

Using conditions identical to those used for cytoscribing with fibronectin, it was found that a mono-clonal antibody to the human EGF receptor could be used to selectively micro-position human cells (FIG. 7). Using a plotter pen filled with 100 micrograms/ml of anti-human EGF receptor monoclonal antibody, it was found that the human cell line A431 bound to sites cytoscribed with monoclonal antibody while the mouse cell line SV-$T_2$ did not adhere. Anti-cell surface monoclonal antibodies thus provide selective reagents with which to micro-position cells.

Figure 8:
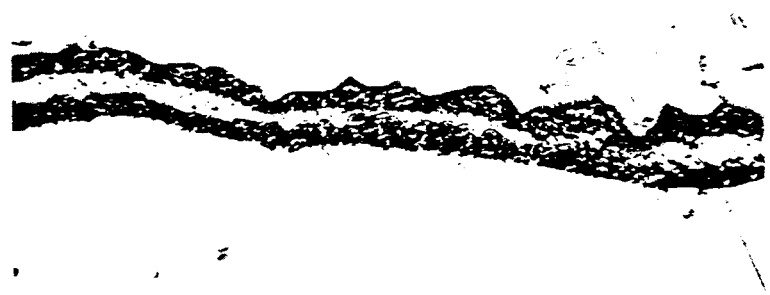
FIG. 8 shows the construction of a three dimensional tissue SV-T2 cells were cultured on thin sheets of collagen prepared by the heat gelation of collagen in a microscope slide mold. Since the cell layers would not attach by being simply pressed together, the layers were glued together with collagen After 1 day in culture, the three-dimensional tissue construct was fixed with neutral buffered formalin and paraffin sections were H&E stained. The section reveals a two cell layer separated by the collagen glue. The bar represents 100 microns.

Construction of a three-dimensional tissue. A procedure for synthesizing three-dimensional tissues is described in same detail above. Briefly, thin sheets of collagen were formed by heat gelatin of collagen in a mold; cells were then cultured on the collagen sheets; and, lastly, the cell layers were glued together with collagen to form a three-dimensional tissue. Sectioning of such constructs demonstrate the formation of three-dimensional tissues (FIG. 8). The procedure above was repeated to generate three-dimensional tissues of many desired thicknesses.

Figure 9:
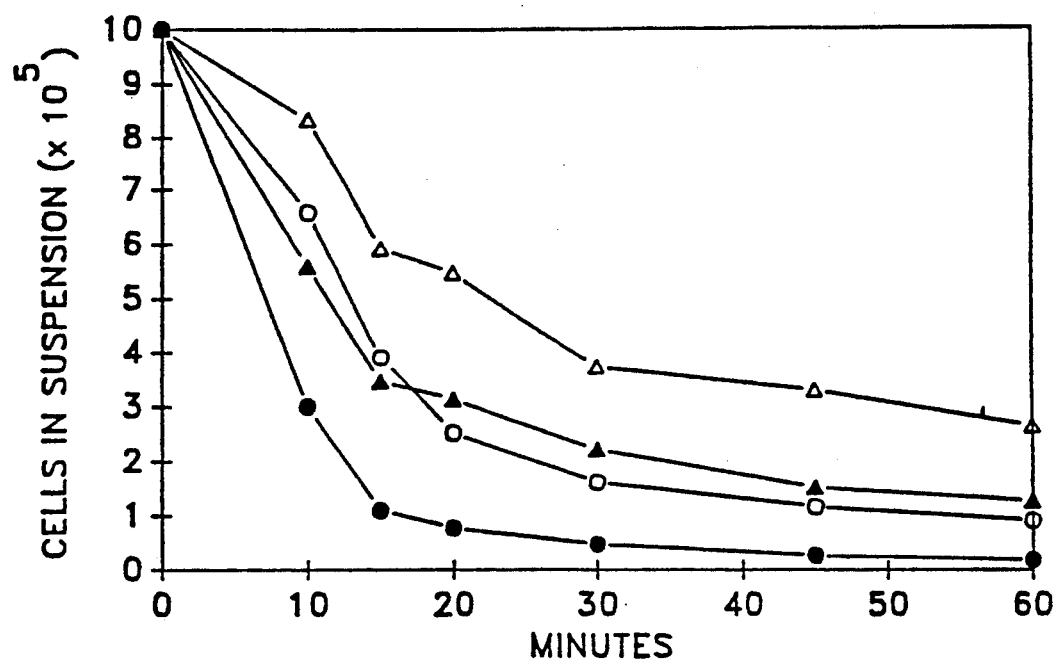
FIG. 9 shows the attachment of cells to the dorsal surface of cells versus plastic substrata. The attachment of single cell suspensions to either confluent monolayers of cells or plastic substrata (Nunc tissue culture dish) was monitored in the presence of 10% newborn calf serum at the times indicated. In the case of both SV-T2 mouse fibroblasts and U20S human osteosarcoma, cell attachment took place less readily on the dorsal surface of cells. (Closed circles) =SV-T2 cell attachment to plastic; (Opened circles) =SV-T2 cell attachment to SV-T2 monolayer; (Closed triangle) =U20S cell attachment to plastic; (Opened triangle) =U20S cell attachment to a U20S monolayer.

Adhesivity of the dorsal surface of cultured cells. During the studies described above, it became apparent that cell sheets would not adhere to each other by simply being pressed together After several hours of contact, cell sheets were found to dissociate upon mild agitation; and, hence, it became necessary to glue the cell sheets together with collagen as described above (FIG. 8). Since single cells would attach to a substratum within minutes under similar conditions, the adhesivity of single cells to cell sheets was investigated and compared to cell-substratum adhesion (FIG. 9).

In the studies described, the attachment of single cells to confluent monolayers of cells or plastic substrata was monitored in the presence of culture medium containing 10% serum. Since optimal cell attachment occurs with as little as 1% serum, the attachment of cells in this study was not limited by the availability of fibronectin. It was found that both SV-T2 fibroblasts and U2OS osteosarcoma cells attached more rapidly to a plastic substratum than to the dorsal surface of cultured cells in the presence of 10% serum (FIG. 9). Thus, the dorsal surface of cultured cells appears to a less adhesive substratum than plastic. The finding that cell sheets will not adhere when the dorsal surfaces of monolayers are pressed together may be explained by the diminished adhesivity of the dorsal surface of cells.

These examples demonstrate several computer directed techniques that permit one to position cells with high precision in virtually any desired pattern. The methods described take advantage of (a) the capabilities of computer graphics and (b) the properties of cell adhesion proteins.

In this example, precise patterns of cells were produced by the precise positioning of a fibronectin solution. While more sophisticated micro-positioning devices are available, the precision of office printers is satisfactory to position a cell to within a cell diameter. For example, the step-and-repeat unit (plotter unit) of a Hewlett Packard plotter is 25 microns. In the case of the photoengraving method described, a minimum image size of 1.5–3 microns is the industry standard for silicon chip manufacturers and submicron resolution can be achieved by variants of the method described here. As illustrated in FIG. 4, photoengraved images of less than the size of a cell are attainable with simple equipment. Thus, the methods described here permit the positioning of cells to within less than a cell diameter.

In addition to micro-positioning methods, the examples of cytoscribing provided here depend on several properties of fibronectin for their success. First, the inability of fibronectin to bind to agarose is herein used to render selected regions of a substratum alternatively adhesive or non-adhesive (FIG. 6). Second, the specificity of the interaction of fibronectin with collagen is herein utilized to form positive and negative patterns of cells (FIG. 4–6). While fibronectin can promote the attachment of cells to 48 man-made substrata (Klebe et al. (1981) J. Cell. Physiol., 109:481), the non-specific binding of fibronectin to man-made materials is competitively blocked by treatment with other proteins. In contrast, the specific interaction of fibronectin with a unique binding site on collagen is not blocked by non-specific protein binding. The above phenomena permit one to selectively block adhesion to specific regions of a substratum while permitting cell attachment to occur normally to other parts of the same substratum.

Based on the specificity of several recently described cell adhesion proteins, it is possible to devise additional strategies for selectively altering the adhesive properties of substrata. For example, the observation that only certain cell types respond adhesively to laminin, chondronectin, and various collagens permits one to construct two dimensional tissues with the ease of plotting a graph in two or more colors. With the aid of the methods described here, three dimensional tissue can be constructed by staking two dimensional tissues in layers. Thus, cytoscribing provides a facile means of establishing precise spatial arrangements within large populations of cells and, thereby, permits new approaches to be made towards the preparation of highly organized tissue-like structures for application to burn victims.

What is claimed is:

1. A combination tissue culture device and an apparatus for the precise positioning of cell adhesion material on the tissue culture device for the cellular arrangement of tissue cultured thereon, the combination comprising:
   (a) a solid support;
   (b) a substratum positioned on said solid support and constructed such that it is separable from said solid support and any tissue cultured thereon;
   (c) container means containing a cell adhesion material; and
   (d) positioning means, connected to the support and in fluid communication with said container means, for positioning said cell adhesion material at selected points within an array on the surface of the substratum.

2. The combination of claim 1 wherein said cell adhesion material is selected from the group consisting of fibronectin, laminin, chondronectin, epinectin, epibolin and uromorulin.

3. The combination of claim 1 wherein the cell adhesion material comprises an antibody having specificity for a cell surface determinant.

4. The combination of claim 1 further comprising a second container means in communication with said positioning means, said second container means containing a biological material to be positioned on said substratum.

5. The combination of claim 1 further comprising means for biologically controlling the environment surrounding the substratum.

6. The combination of claim 1 wherein said substratum is selected from the group consisting of collagen, polylactide, pyrex glass, carnmauba wax, silicone aluminum, polytetrafluoroethylene, polyvinyl acetate, polyvinyl chloride and polystyrene.

7. The combination of claim 1 wherein the substratum comprises collagen in the form of a wafer or sheet.

8. The combination of claim 1 wherein said positioning means comprises:
   (a) a housing constructed so as to receive a flow of the cell adhesion material from the container means and depositing the material on the substratum, the housing having at least one metered pore through which the material may flow onto the substratum; and
   (b) data processing means for precisely locating the housing at points within the array.

9. The combination of claim 8 wherein the housing has a plurality of metered pores and the positioning means further comprises data processing means for metering the flow of the material through the pores.

10. The combination of claim 9 wherein the housing comprises an ink jet printer or graphics plotter head.

11. The combination of claim 1 wherein the positioning means is movable to selected points with a 2-dimensional array.

12. The combination of claim 1 wherein the positioning means is movable to selected points within a 3-dimensional array.

13. A combination tissue culture device and an appartus for the precise positioning of living cells on a the tissue culture device for the cellular arrangement of tissue cultured thereon, the combination comprising:
   (a) a solid support;
   (b) a substratum positioned on said solid support and constructed such that it si separable from said solid support and any tissue cultured thereon;
   (c) container means containing living cells; and
   (d) positioning means, connected to the support and in fluid communication with said container means, for positioning said living cells at selected points within an array on the surface of the substratum.

* * * * *

UNITED STATES PATENT AND TRADEMARK OFFICE
CERTIFICATE OF CORRECTION

PATENT NO. : 5,108,926

DATED : April 28, 1992

INVENTOR(S) : Robert J. Klebe

It is certified that error appears in the above-identified patent and that said Letters Patent is hereby corrected as shown below:

In claim 13, line 45, column 16, please delete --appartus-- and insert therefor "apparatus."

In claim 13, line 51, column 16, please delete --si-- and insert therefor "is".

Signed and Sealed this

Thirteenth Day of July, 1993

Attest:

MICHAEL K. KIRK

*Attesting Officer*   Acting Commissioner of Patents and Trademarks